(12) United States Patent
Farley

(10) Patent No.: US 11,311,416 B2
(45) Date of Patent: *Apr. 26, 2022

(54) HIGH SPEED PNEUMATIC VALVE

(71) Applicant: Alcon Inc., Fribourg (CH)

(72) Inventor: Mark Harrison Farley, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 394 days.

This patent is subject to a terminal disclaimer.

(21) Appl. No.: 16/460,419

(22) Filed: Jul. 2, 2019

(65) Prior Publication Data

US 2019/0321224 A1    Oct. 24, 2019

Related U.S. Application Data

(63) Continuation of application No. 15/091,686, filed on Apr. 6, 2016, now Pat. No. 10,383,766.
(Continued)

(51) Int. Cl.
*A61F 9/007* (2006.01)
*F16K 11/085* (2006.01)
(Continued)

(52) U.S. Cl.
CPC .......... *A61F 9/00763* (2013.01); *A61B 17/00* (2013.01); *A61M 39/227* (2013.01); *F16K 11/0856* (2013.01); *A61B 2017/00544* (2013.01)

(58) Field of Classification Search
CPC ...... A61B 17/3203; A61B 2017/32035; A61B 2017/00535; A61B 2017/00539; A61B 2017/00544; A61B 2017/00548; A61B 17/320068; A61B 17/320092; A61B 17/320016; A61B 17/32002;
(Continued)

(56) References Cited

U.S. PATENT DOCUMENTS

| 2003/0000009 A1* | 1/2003 | Brennan ............... F16K 11/085 4/541.1 |
| 2014/0171993 A1* | 6/2014 | Lynn ................... A61F 9/00763 606/170 |

(Continued)

FOREIGN PATENT DOCUMENTS

| DE | 102006011580 B3 * | 10/2007 | .......... F16K 11/0856 |
| GB | 324239 A | 1/1930 | |
| JP | 2013006123 A | 1/2013 | |

*Primary Examiner* — Katherine H Schwiker

(57) ABSTRACT

A pneumatic valve directs pressurized air to and air exhaust from a surgical implement, such as a dual actuation vitreous probe. The pneumatic valve includes an axially symmetric valve body configured to rotate from a first position, in which the pneumatic valve places a first port of the surgical implement in fluid communication with the pressurized air and a second port of the surgical implement in fluid communication with the air exhaust, to a second position, in which the pneumatic valve places the first port in fluid communication with the air exhaust and the second port in fluid communication with the pressurized air, and back to the first position, in one rotational direction. As such, the axially symmetric valve body continuously rotates in one rotational direction to alternate the pressurized air and the air exhaust between the two ports of the surgical implement to drive the dual actuation operation.

18 Claims, 8 Drawing Sheets

Related U.S. Application Data

(60) Provisional application No. 62/146,595, filed on Apr. 13, 2015.

(51) Int. Cl.
    *A61B 17/00*    (2006.01)
    *A61M 39/22*    (2006.01)

(58) Field of Classification Search
CPC ......... A61B 2017/320069; A61B 2017/32007; A61B 2017/320072; A61B 2017/320073; A61B 2017/320074; A61B 2017/320075; A61B 2017/320077; A61B 2017/320078; A61B 2017/32008; A61B 2017/320082; A61B 2017/320084; A61B 2017/320088; A61B 2017/320089; A61B 2017/32009; A61B 2017/320093; A61B 2017/320094; A61B 2017/320095; A61B 2017/320098; A61B 2017/320024; A61B 2017/320028; A61B 2017/320032; A61B 17/00; A61F 9/00763; A61F 9/00736; A61F 9/00745; A61F 9/00754; A61F 9/007; A61M 39/227; A61M 39/228; A31M 2039/229; F61K 11/085; F61K 11/0853; F61K 11/0856; F61K 11/07; F61K 11/0716; F16F 5/0407; F02M 26/30; F02M 26/26; F02M 26/71; Y10T 137/86645; Y10T 137/86654; Y10T 137/86541; Y10T 137/86566; F16K 11/085; F16K 11/0856

See application file for complete search history.

(56) References Cited

U.S. PATENT DOCUMENTS

| | | | | |
|---|---|---|---|---|
| 2014/0171995 | A1* | 6/2014 | McDonell | A61F 9/00763 |
| | | | | 606/170 |
| 2014/0276369 | A1* | 9/2014 | Banko | A61M 1/774 |
| | | | | 604/22 |
| 2016/0223090 | A1* | 8/2016 | G. R. | F15B 1/26 |

\* cited by examiner

HIGH SPEED PNEUMATIC VALVE

This application is a continuation application of U.S. Non-Provisional application Ser. No. 15/091,686, filed Apr. 6, 2016, which is entitled "High Speed Pneumatic Valve" and claims priority to U.S. Provisional Application Ser. No. 62/146,595 filed Apr. 13, 2015, which is entitled "High Speed Pneumatic Valve" (U.S. Non-Provisional application Ser. No. 15/091,686, filed Apr. 6, 2016, claimed the benefit of priority of U.S. Provisional Application Ser. No. 62/146,595 filed Apr. 13, 2015). Both U.S. Non-Provisional application Ser. No. 15/091,686 and U.S. Provisional Application Ser. No. 62/146,595 are hereby incorporated by reference in their entirety as though fully and completely set forth herein.

BACKGROUND

The devices, systems, and methods disclosed herein relate generally to pneumatic valves, and more particularly, to pneumatic valves utilized in a vitreoretinal surgical console.

A vitreoretinal surgical console typically includes pneumatic valves and manifolds to provide reciprocating cutter motion in a dual acting vitreous probe. The pneumatic valves and manifolds supply actuation pressure and venting selectively to each side of a diaphragm in an alternating sequence to provide the dual actuation operation. The pneumatic valve switches between a supply pressure and an air exhaust through a pair of pneumatic tubes connected between the probe and the valve manifold. As shown in FIG. 7, a conventional pneumatic valve 710 is provided to switch between a first position, in which the pressurized air supply 720 is connected to port A and the air exhaust 730 is connected to port B, and a second position, in which the pressurized air supply 720 is supplied to port B and the air exhaust 730 is connected to port A. In between the first position and the second position, the conventional pneumatic valve is in a transition state.

Typically, a reciprocating spool or poppet is provided to switch the pneumatic valve 710 back and forth between the first position and the second position to alternately open and close ports in the valve body that are routed to fittings in the manifold and connected to tubes leading to the vitreous probe 750. The reciprocating movement of the spool or poppet is typically induced electromechanically at high repetition rates corresponding to the cut rate of the vitreous probe. For example, the reciprocation rate may typically exceed 5,000 cuts per minute (83 Hz). The high acceleration forces associated with rapid reversals between each reciprocating motion may cause vibration and noise. Further, the sliding seals introduce friction and wear. Faster repetition rates are associated with improved patient benefits by means of reduced traction forces transmitted to the retina.

The present disclosure is directed to devices, systems, and methods that address one or more of the disadvantages of the prior art, while enabling patient benefits provided by faster repetition.

SUMMARY

In an exemplary aspect, the present disclosure is directed to a pneumatic valve for a surgical system. The pneumatic valve is configured to direct a pressurized fluid to and a fluid exhaust from a surgical implement of the surgical system. The pneumatic valve includes an axially symmetric valve body and a housing configured to accommodate the axially symmetric valve body. The axially symmetric valve body is configured to rotate within the housing from a first position, in which the pneumatic valve places a first port of the surgical implement in fluid communication with the pressurized air and the second port of the surgical implement in fluid communication with the fluid exhaust, to a second position, in which the pneumatic valve places the first port of the surgical implement in fluid communication with the fluid exhaust and the second port of the surgical implement in fluid communication with the pressurized fluid, and back to the first position, in one rotational direction.

In an aspect, the axially symmetric valve body includes a first connection channel formed through the axially symmetric valve body and configured to place the first port and the pressurized fluid in fluid communication when the axially symmetric valve body is in the first position, and a second connection channel formed through the axially symmetric valve body and configured to place the second port and the fluid exhaust in fluid communication when the axially symmetric valve body is in the first position. The axially symmetric valve body also includes a third connection channel formed through the axially symmetric valve body and configured to place the first port and the fluid exhaust in fluid communication when the axially symmetric valve body is in the second position, and a fourth connection channel formed through the axially symmetric valve body and configured to place the second port and the pressurized fluid in fluid communication when the axially symmetric valve body is in the second position.

In another aspect, the axially symmetric valve body includes flow grooves formed on a circumferential surface of the axially symmetric valve body and extending from openings of one or more of the connection channels. The flow grooves define opening or closing timing sequences of the one or more connection channels as the axially symmetric valve body rotates. A close tolerance air gap is provided between the circumferential surface of the axially symmetric valve body and an inner wall of the housing to form a frictionless air bearing when the axially symmetric valve body rotates in the housing. A radial- and tilt-wise compliant torque coupling may be provided between the rotating shaft and valve body to facilitate self-centering of the valve body in the housing and maintenance of a substantially uniform air bearing thickness within the close-tolerance air gap. The close-tolerance air gap combined with air baffles at the opening in the housing in the area of shaft entry creates resistance to air leakage. Thus, the axially symmetric valve body may not require any air seals.

In another exemplary aspect, the present disclosure is directed to a surgical system. The surgical system includes a surgical implement with a first port and a second port, a pressurized fluid supplying device configured to supply a pressurized fluid to the surgical implement, a fluid exhaust manifold configured to direct a fluid exhaust from the surgical implement, and a pneumatic valve. The pneumatic valve is configured to rotate from a first position, in which the pneumatic valve places the first port of the surgical implement in fluid communication with the pressurized fluid supply device and the second port of the surgical implement in fluid communication with the fluid exhaust manifold, to a second position, in which the pneumatic valve places the first port of the surgical implement in fluid communication with the fluid exhaust manifold and the second port of the surgical implement in fluid communication with the pressurized fluid supplying device, and back to the first position, in one rotational direction. In an aspect, the surgical implement is a dual actuation vitreous probe and a rotational speed of the pneumatic valve corresponds to a cutting rate of the dual actuation vitreous probe. A drive shaft coupled to the valve with radial and tilt compliance also is provided in the surgical system to rotate the pneumatic valve.

In still another exemplary aspect, the present disclosure is directed to a method including: providing a pneumatic valve in a surgical system to direct a pressurized fluid to and a fluid exhaust from a surgical implement; and rotating an axially symmetric valve body of the pneumatic valve in one rotational direction to move the axially symmetric valve body from a first position, in which the pneumatic valve places a first port of the surgical implement in fluid communication with the pressurized fluid and the second port of the surgical implement in fluid communication with the fluid exhaust, to a second position, in which the pneumatic valve places the first port of the surgical implement in fluid communication with the fluid exhaust and the second port of the surgical implement in fluid communication with the pressurized fluid, and back to the first position.

In an aspect, the surgical implement is a dual actuation vitreous probe, and the method further includes adjusting a rotational speed of the axially symmetric valve body to adjust a cutting rate of the dual actuation vitreous probe. The axially symmetric valve body is rotated through a radial- and tilt-wise compliant coupling by a driving shaft of the surgical system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
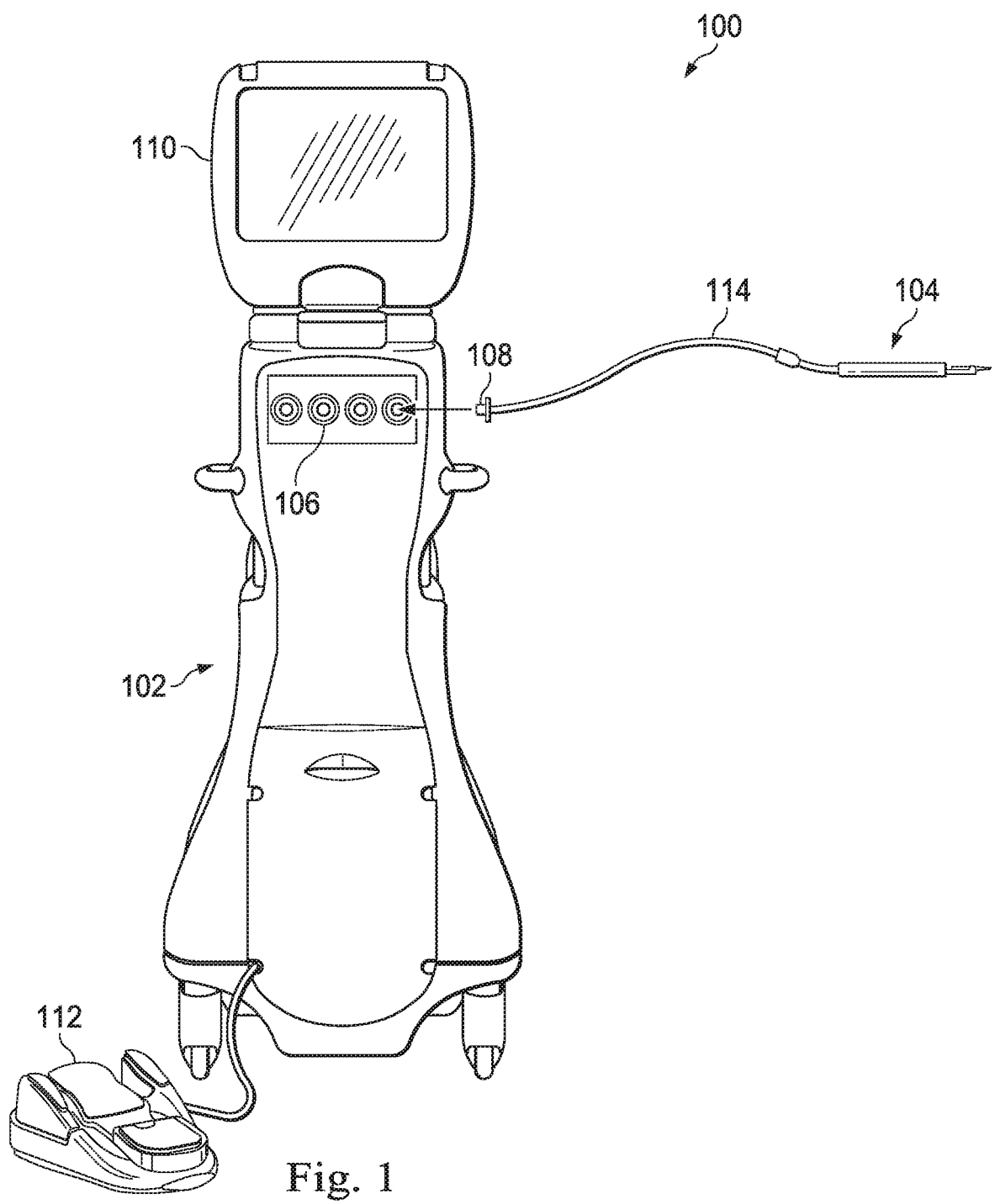
FIG. 1 illustrates a plan view of an exemplary surgical system according to one embodiment consistent with the principles of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The devices, systems, and methods described herein provide a pneumatic valve configured to direct a pressurized air to and an air exhaust from a surgical implement, such as a dual actuation vitreous probe. In particular, the pneumatic valve may include an axially symmetric valve body configured to rotate from a first position, in which the pneumatic valve places a first port of the surgical implement in fluid communication with the pressurized air and the second port of the surgical implement in fluid communication with the air exhaust, to a second position, in which the pneumatic valve places the first port of the surgical implement in fluid communication with the air exhaust and the second port of the surgical implement in fluid communication with the pressurized air, and back to the first position, in one rotational direction. As such, the axially symmetric valve body continuously rotates in one rotational direction to alternate fluid communication of the pressurized air and the air exhaust between the first port and the second port of the surgical implement to drive the dual actuation operation.

FIG. 1 illustrates an exemplary surgical system, generally designated 100. The surgical system 100 may include a surgical utility supplying device 102 with an associated display screen 110 showing data relating to system operation and performance during a surgical procedure. The surgical system 100 also may include a surgical implement 104 configured to be connected to the surgical utility supplying device 102 via a surgical utility connector 108. The surgical utility supplying device 102 may supply various utility, such as imaging light, compressed air, vacuum, pressurized liquid, or the like, to various kinds of surgical implements. The surgical utility supplying device 102 also may include an atmosphere exhaust manifold configured to direct air exhaust to the atmosphere. For example, the surgical utility supplying device 102 may supply pressurized air to and direct air exhaust from a dual actuation surgical vitrectomy probe.

A user, e.g., a surgeon, may perform surgeries using the surgical implements. The surgical utility supplying device 102 may include one or more utility ports 106 each configured to output a certain type of utility. The utility may be output from the utility port 106 to the surgical utility connector 108 and be carried by a tube fiber, hose, or cable (referenced herein as cable 114) to the surgical implement 104. The exemplary embodiment of the surgical system 100 in FIG. 1 also may include a foot pedal 112 connected to the surgical system 100 for controlling the dispensing of utility from the surgical system 110. In some embodiments, a user controls the dispensing of the utility by selectively pressing and releasing the foot pedal 112.

Figure 2:
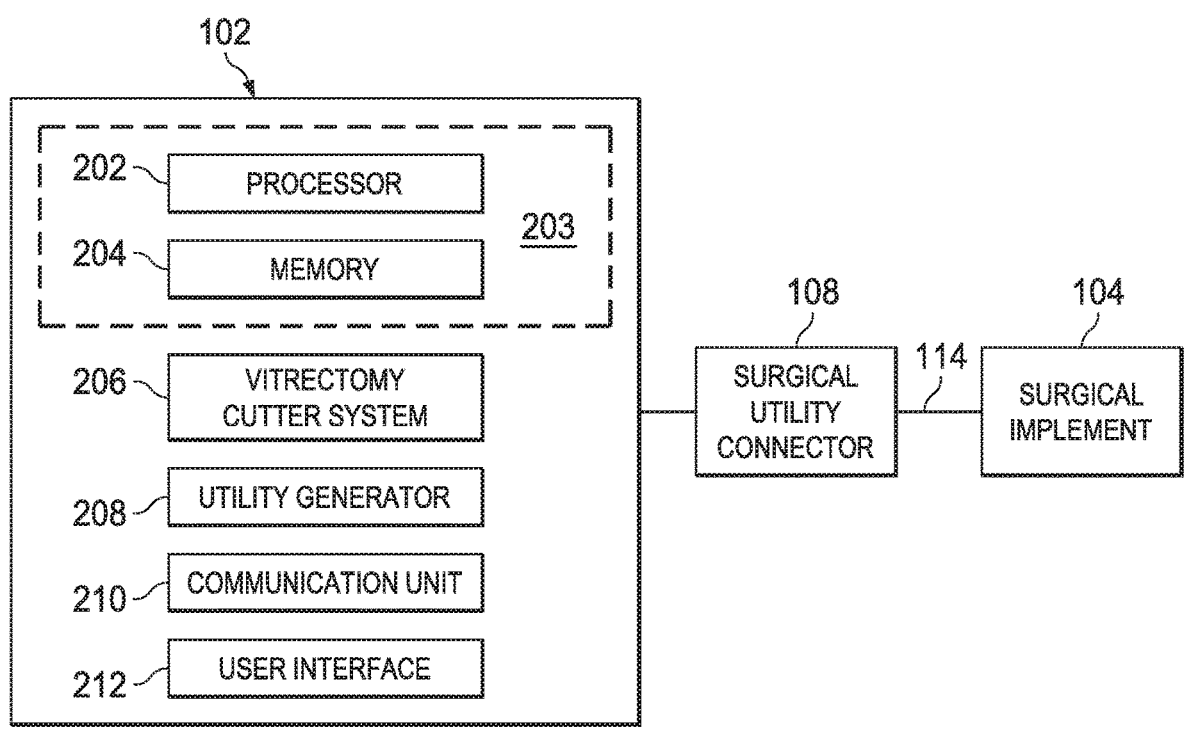
FIG. 2 is a block diagram of the surgical system of FIG. 1 showing various components of the surgical system according to one embodiment consistent with the principles of the present disclosure.

FIG. 2 illustrates a block diagram of an exemplary surgical utility supplying device, e.g., the surgical utility supplying device 102. The surgical utility supplying device 102 may include a controller 203. The controller 203 may include a processor 202 configured to perform calculation and determination processes for controlling various operations of the surgical utility supplying device 102. The processor 202 may receive various signal inputs and make various determinations based on the signal inputs. For example, the processor 202 may control a rotational speed of a pneumatic valve to adjust a cutting speed of a vitreous probe. The processor 202 also may control the display screen 110 (FIG. 1) to display information regarding the operations of the surgical utility supplying device 102 to convey information to the user.

The controller 203 also may include a memory 204 configured to store information permanently or temporarily for various operations of the surgical utility supplying device 102. For example, the memory 204 may store programs that may be executed by the processor 202 to perform various functions of the surgical utility supplying device 102. The memory 204 also may store various data relating to operation history, user profile or preferences, various operation and surgical settings, and the like. Programs and information stored in the memory 204 may be continuously updated to provide customization and improvement in the operation of the surgical utility supplying device 102. The memory 204 also may include programs and information relating to operational parameters implemented based on the connection status of the surgical utility connector 108 and the utility ports 106.

The surgical utility supplying device 102 also may include a vitrectomy cutter system 206 configured to provide functions for vitrectomy surgeries. In particular, the vitrectomy cutter may include a pneumatic valve that selectively directs a pressurized air and an atmosphere exhaust to a vitreous surgical implement.

The surgical utility supplying device 102 may include a utility generator 208. The utility generator 208 may include motors, light emitting devices, generators, pumps, vacuums, compressors, and the like that may generate various utilities, such as pressured liquid, compressed air, vacuum, imaging light, and the like. In some embodiments, the utility generator 208 is connected to an external utility source to receive utility externally. For example, the utility generator 208 may be connected to a vacuum source or an air compressor to receive vacuum or compressed air. The utility generator 208 may supply various utilities to respective utility ports 106.

The surgical utility supplying device 102 may include a communication unit 210. The communication unit 210 may include various communication devices, such as an Ethernet card, Wi-Fi communication device, telephone device, digital I/O (Input/Output) ports or the like, that may allow the surgical utility supplying device to send and receive information to and from other devices. For example, the communication unit 210 may receive input from other surgical devices to coordinate a surgical operation. In another example, the communication unit 210 may transmit and receive messages or notifications, such as email, text, or other messages or notifications to a user's mobile device to notify certain information to the user.

The surgical utility supplying device 102 also may include a user interface 212. The user interface 212 may include user input devices, such as a keyboard, a touch screen, the foot pedal 112, a mouse, a microphone, or the like that allow a user to input instructions to the surgical utility supplying device 212. For example, the user may enter parameters for a utility and operate the foot pedal 112 to dispense the utility to the surgical implement 104. The user interface 212 also may include user output devices, such as the display screen 110, an audio speaker, LED (Light-Emitting Diode) lights, or other visual or tactile signals that convey information to a user. Thus, the user interface 212 enables a user to interact with the surgical utility supplying device 102 during surgical operations.

The surgical utility supplying device 102 or the surgical implement 104 may include a valve that regulates the flow of a utility, such as a fluid, from the surgical utility supplying device 102 to the surgical implement 104. As will be discussed in the description below, the valve may alternately provide a driving fluid and an exhaust in a manner that drives the surgical implement 104.

Figure 3A:
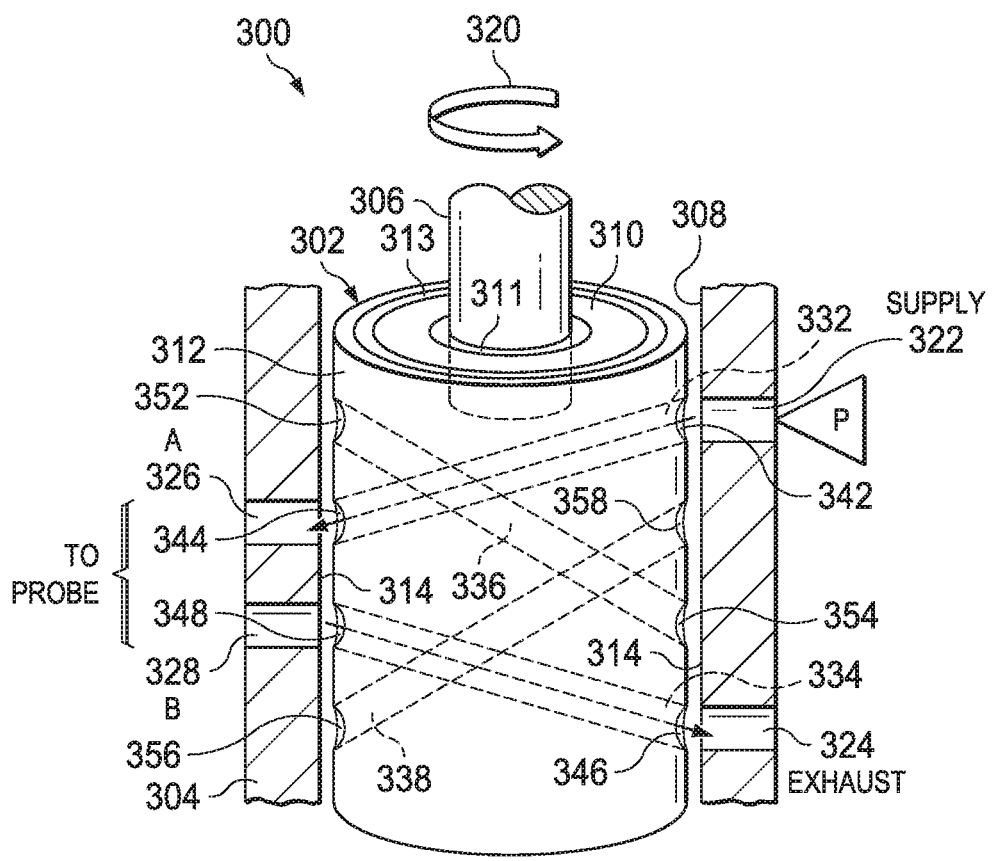
FIGS. 3A and 3B are illustrations showing perspective views of a pneumatic valve according to one embodiment consistent with the principles of the present disclosure.
Figure 3B:
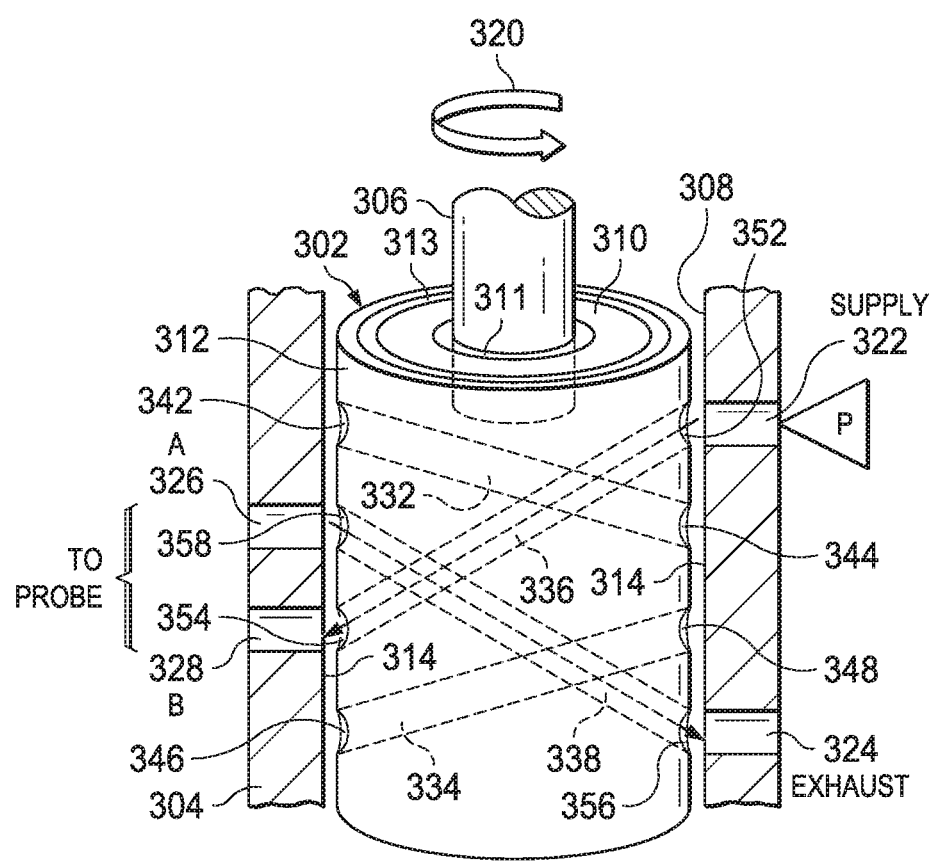

FIGS. 3A and 3B are illustrations showing perspective views of a pneumatic valve 300 according to one embodiment consistent with the principles of the present disclosure. FIG. 3A illustrates a pneumatic valve 300 in a first position or a first state, and FIG. 3B illustrates the pneumatic valve 300 in a second position or a second state. The pneumatic valve 300 may include an axially symmetric valve body 302 accommodated in a housing 304. In particular, the axially symmetric valve body 302 may rotate within a chamber 308 of the housing 304. A drive shaft 306 may be provided to rotate the axially symmetric valve body 302. In particular, the drive shaft 306 may couple, by means of a radial- and tilt-wise compliant coupling 311, to a drive shaft engagement interface 310 of the axially symmetric valve body 302. The drive shaft 306 may rotate the axially symmetric valve body 302 in one rotational direction 320. A close-tolerance air gap (e.g., with a gap spacing of less than 0.005 inches) may be provided between a circumferential surface 312 of the axially symmetric valve body 302 and an inner wall 314 of the chamber 308 as facilitated between the compliant coupling 311. As such, when the axially symmetric valve body 302 rotates, a frictionless air bearing may be generated via a close-fitting tolerance between the axially symmetric valve body 302 and the inner wall 314. Other gap spacings are also contemplated (e.g., less than 0.1 inches, less than 0.01 inches, less than 0.001 inches, etc.) The close-fitting tolerance may be further maintained by one or more concentric air baffles 313 between the axially symmetric valve body which restrict flow leakage, thereby eliminating the need for dynamic seals and the corresponding friction, wear, noise and vibration during the operation of the pneumatic valve 300.

A pressurized air opening 322 may be formed in the inner wall 314 of the housing 304. The pressurized air opening 322 may be in fluid communication with a pressurized air supplying device, such as a compressed air source or a vacuum source. Thus, the pressurized air opening 322 provides the pressurized air to the pneumatic valve 300. An air exhaust opening 324 also may be formed in the inner wall 314 of the housing 304. The air exhaust opening 324 may be in fluid communication with an air exhaust manifold that directs air exhaust from the pneumatic valve 300 to the atmosphere.

A port opening 326 (port "A") and a port opening 328 (port "B") may be formed in the inner wall 314 of the housing 304. The port openings 326 and 328 are connected to utility input ports of the surgical implement 104 respectively to direct pressurized air to and air exhaust from the surgical implement 104. For example, port opening 326 may be in fluid communication with one side of an actuation diaphragm at the surgical implement 104 while port opening 328 may be in fluid communication with the other side of the actuation diaphragm at the surgical implement 104. A dual actuation operation may be implemented at the surgical implement 104 by alternating the supply of pressurized air and the output of the air exhaust between the two sides of the actuation diaphragm via port openings 326 and 328. The dual actuation may provide a cutting function at the surgical implement 104, such as a vitreous probe.

The axially symmetric valve body 302 may include a channel 332 formed therethrough. The axially symmetric valve body 302 also may include a channel 334 formed therethrough. The channel 332 may have a channel opening 342 and a channel opening 344 and the channel 334 may have a channel opening 346 and a channel opening 348 formed on the circumferential surface 312 of the axially symmetric valve body 302. The pneumatic valve 300 rotates about its axis so that the valve body 302 passes the first position or first state in FIG. 3A, passes the second position or second state in FIG. 3B, and continues to rotate back to the first position or first state in FIG. 3A. When in the first position or the first state, as shown in FIG. 3A, the channel opening 342 of the channel 332 may align with the pressurized air opening 322 and the channel opening 344 of the channel 332 may align with the port opening 326. Similarly, the channel opening 346 of the channel 334 may align with the air exhaust opening 324 and the channel opening 348 of the channel 334 may align with the port opening 328. Thus, the channel 332 may place the pressurized air opening 322 in fluid communication with the port opening 326 and the channel 334 may place the air exhaust opening 324 in fluid communication with the port opening 328.

The axially symmetric valve body 302 further may include a channel 336 and a channel 338 formed therethrough. The channel 336 may have a channel opening 352 and a channel opening 354 and the channel 338 may have a channel opening 356 and a channel opening 358 formed on the circumferential surface 312 of the axially symmetric valve body 302. When the pneumatic valve 300 is in the second position or the second state, as shown in FIG. 3B, the channel opening 352 of the channel 336 may align with the pressurized air opening 322 and the channel opening 354 of the channel 336 may align with the port opening 328. Similarly, the channel opening 356 of the channel 338 may align with the air exhaust opening 324 and the channel opening 358 of the channel 338 may align with the port opening 326. Thus, the channel 336 may place the pressurized air opening 322 in fluid communication with the port opening 328 and the channel 338 may place the air exhaust opening 324 in fluid communication with the port opening 326. When the axially symmetric valve body 302 is in a transitional position between the first and the second positions, the circumferential surface 312 of the axially symmetric valve body 302 may block or close the air supply opening 322, the air exhaust opening 324, and the port openings 326 and 328. Although the various channels 332, 334, 336, 338 are shown as crossing in FIGS. 3A and 3B, in preferred embodiments, the channels do not intersect, thus maintaining the integrity of the flow paths.

Figure 4:
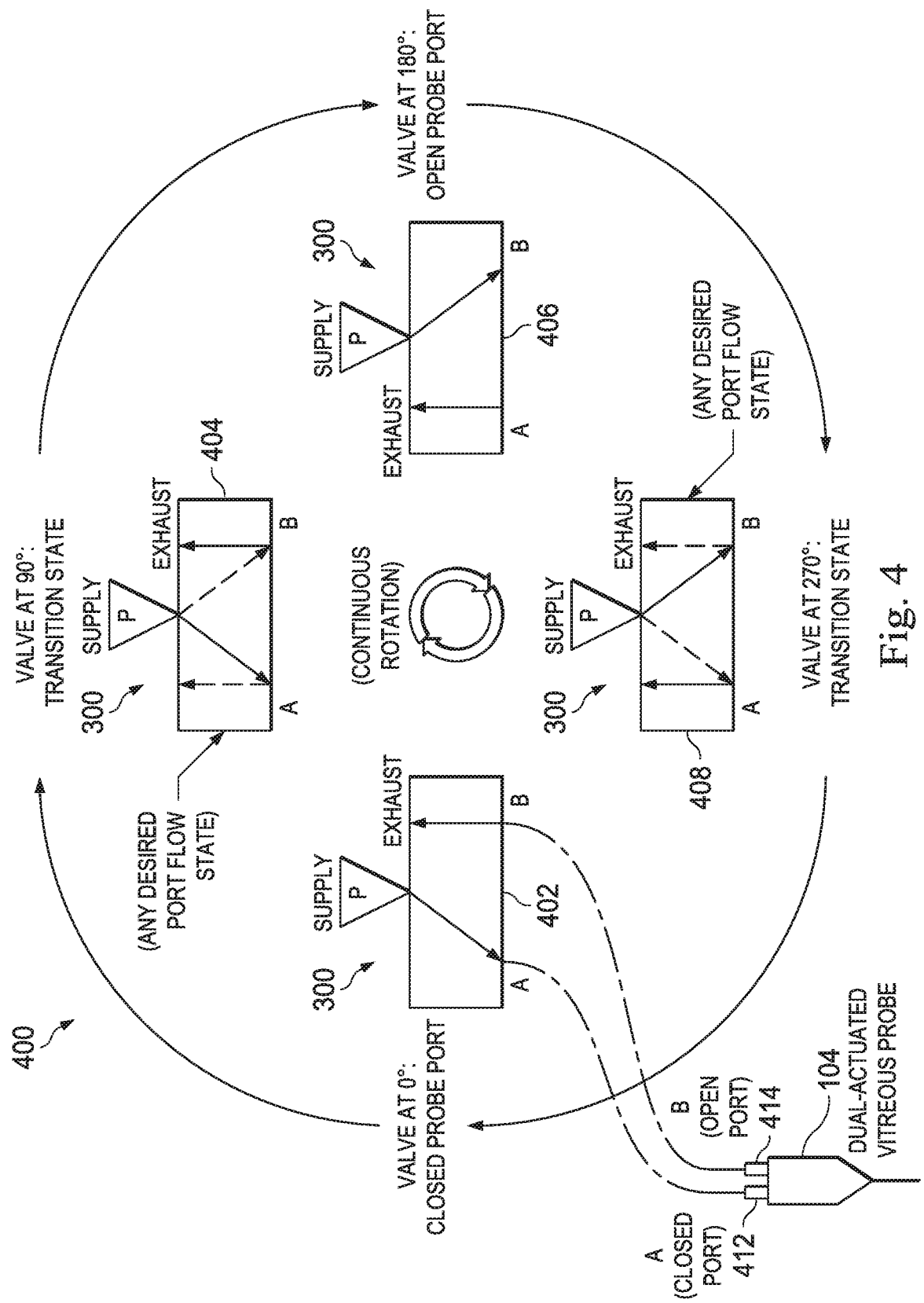
FIG. 4 is a diagram showing an operation of a pneumatic valve according to one embodiment consistent with the principles of the present disclosure.

The drive shaft 306 may continuously rotate the axially symmetric valve body 302 in one rotational direction 320 to continuously alternate the pneumatic valve 300 between the first position, as shown in FIG. 3A, and the second position, as shown in FIG. 3B. FIG. 4 is a diagram showing an operation 400 of the pneumatic valve 300 according to one embodiment consistent with the principles of the present disclosure. As shown in FIG. 4, the pneumatic valve 300 selectively supplies a pressurized air to and directs an air exhaust from an input port 412 (port "A") and an input port 414 (port "B") of the surgical implement 104, such as a dual-actuated vitreous probe. At phase 402, the pneumatic valve 300 is in the first position to supply the pressurized air to the input port 412 and to direct the air exhaust from the input port 414. The pneumatic valve 300 may be in the zero degree rotational position at phase 402 or at the first position.

As the pneumatic valve 300 rotates from a zero-degree rotational position in phase 402 to a 90-degree rotational position in phase 404, the pneumatic valve 300 may rotate from the first position to a transitional position. The pressurized air or the air exhaust may or may not be in fluid communication with the input ports 412 and 414 in the transitional position of phase 404 based on the design structure of the pneumatic valve, as will be discussed later. As the pneumatic valve 300 rotates from the 90-degrees rotational position in phase 404 to a 180-degree rotational position in phase 406, the pneumatic valve 300 may rotate from the transitional position to the second position. In the second position or phase 406, the pneumatic valve 300 may place the pressurized air in communication with input port 414 and the air exhaust in fluid communication with input port 412.

The pneumatic valve 300 then rotates from the 180-degree rotational position in phase 406 to a 270-degree rotational position in phase 408, the pneumatic valve 300 may rotate from the second position to another transitional position. The pressurized air or the air exhaust may or may not be in fluid communication with the input ports 412 and 414 in the transitional position of phase 408 based on the design structure of the pneumatic valve, as will be discussed later. After phase 408, the pneumatic valve 300 may rotate from the 280-degree rotational position in phase 408 back to the zero-degree rotational position in phase 402. Thus, the pneumatic valve 300 rotates from the second position back to the first position in the same rotational direction.

The pneumatic valve 300 may continuously rotate in one rotational direction to switch between the first position and the second position. As such, the pneumatic valve 300 may alternate the supply of the pressurized air and the release of the air exhaust to the two input ports 412 and 414 of the surgical implement 104. This may generate the dual actuation at the surgical implement 104. The actuation rate, such as a cutting rate, at the surgical implement 104 may correspond to the rate of rotation of the pneumatic valve 300.

The rotational pneumatic valve 300 may reduce noise and vibration, as compared with the traditional reciprocating valve. Further, the frictionless air bearing between the axially symmetric valve body 302 and the housing 304 may reduce friction and wear. In addition, the rotational pneumatic valve 300 may provide for higher speed of actuation with higher rotational speed.

Figure 5A:
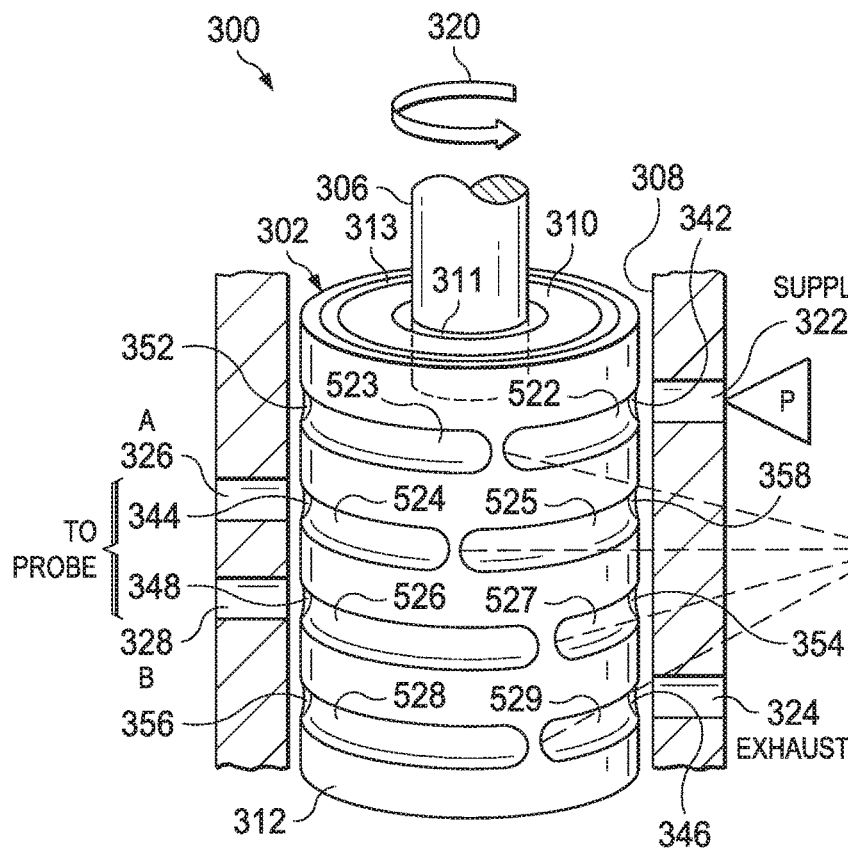
FIG. 5A is an illustration showing a perspective view of a pneumatic valve according to another embodiment consistent with the principles of the present disclosure.

FIG. 5A is an illustration showing a perspective view of a pneumatic valve according to another embodiment consistent with the principles of the present disclosure. Many of the features are the same as those discussed above with respect to FIGS. 3A and 3B, and are not re-described. The embodiment shown in FIG. 5A, however, includes a plurality of flow grooves formed on the circumferential surface 312 of the axially symmetric valve body 302. The exemplary embodiment in FIG. 5A includes a flow groove corresponding to each channel opening. For example, the axially symmetric valve body 302 in FIG. 5A includes flow grooves 522, 523, 524, 525, 526, 527, 528, 529. Each flow groove 522, 523, 524, 525, 526, 527, 528, 529 extends from or overlaps with a respective channel opening 342, 352, 344, 358, 348, 354, 356, 346. Each flow groove 522, 523, 524, 525, 526, 527, 528, 529 operates to extend its respective channel opening into a longer circumferential groove, rather than only a circular opening. For example, the flow groove 522 extends the channel opening 342 to place the pressurized air opening 322 in fluid communication with channel 332 for a circumferential length along the valve body 302 that is greater than the diameter or width of the channel opening 342 by itself. Flow grooves, therefore, may be formed for and extend from one or more of the corresponding channel openings of the channels 332, 334, 336, and 338 shown in FIGS. 3A and 3B.

Each flow groove may extend from or overlap its corresponding channel opening. As such, during a rotational cycle of the valve body 302, the flow groove may extend the amount of time that the channel opening is in fluid communication with the one of the air openings 322, 324 and the port openings 326, 328. For example, the channel opening 342 is in fluid communication with the supply air opening 322 for the entire length of time that the flow groove 522 is aligned with the supply port 322 during a valve body rotation or cycle. As such, the channel opening 342 may be in fluid communication with the pressurized air opening 322 not only when the axially symmetric valve body 304 is in the first position (FIG. 3A) in which the channel opening 342 is aligned with the pressurized air opening 322, but also after the axially symmetric valve body 304 moves away from the first position and the pressurized air opening 322 is aligned with a portion of the flow groove 522. Similarly, a flow groove 524 may be formed to extend from the channel opening 344 of the channel 332 to extend the time during a rotational cycle that the channel opening 344 is in fluid communication with the port opening 326. Each flow groove may operate in this manner. This allows the channel 332 (FIGS. 3A and 3B) to continue to place the pressurized air in communication with port opening 326 for an extended period of time after the pneumatic valve 300 moves away from the first position (FIG. 3A), such as in a transitional position between the first position and the second position (FIG. 3B).

The flow grooves may be provided for one or more channel openings on the axially symmetric valve body 302. For example, as shown in FIG. 5A, each of the channel openings 342, 344, 346, 348, 352, 354, 356, and 358 may have a flow groove extending therefrom. The length of the flow grooves may define the length of time that the channel openings are in fluid communication with the air openings 322, 324 and the port openings 326, 328. For example, the longer a flow groove is, the longer the corresponding channel opening provides fluid communication during a single rotation or cycle of the valve body 302. This may provide flexibility to implement multi-port configurations with overlapping switch points to optimize dynamic actuation response. For example, various flow groove configurations may provide for independently timed or overlapping manifold and probe connections for each port.

The embodiment in FIG. 5A includes multiple flow grooves disposed at each axial location along the body. For example, the flow grooves 522 and 523 are formed along the same axial location along the rotational axis of the valve body 102. Likewise, in this example, flow grooves 524, 525, flow grooves 526, 527, and flow grooves 528, 529 each respectively share an axial location. Because of this, each flow groove may extend less than 180 degrees about the circumference of the valve body 302. However, the valve body is not so limited and other embodiments may have flow grooves that extend greater than 180 degrees about the circumference of the valve body 302. Furthermore, in some embodiments, the flow grooves are axially offset from each other, such that only a single flow groove may be disposed at a single axial location. This may provide additional latitude when determining how long to make the flow groove. FIG. 5A also shows that different flow grooves may have ends that are circumferentially offset from one another. For example, the end of flow groove 523 is circumferentially offset from the end of the adjacent flow groove 524. This allows the communication with the ports 322, 324, 326, 328 to start and stop in a timed sequence that may be selected based on the application and desired operating parameters of the valve.

Figure 5B:
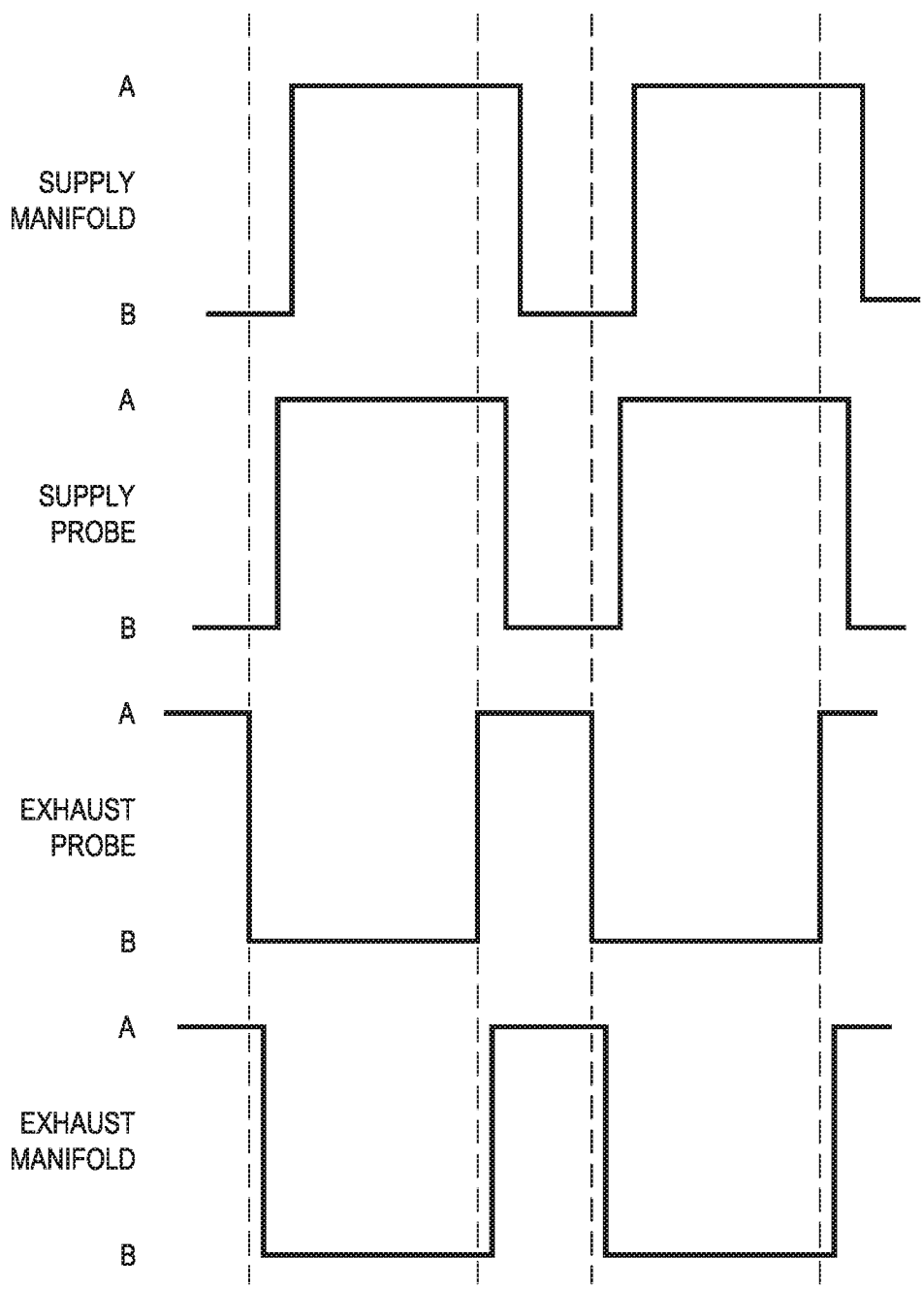
FIG. 5B is a diagram showing timing sequences of an operation of a pneumatic valve according to one embodiment consistent with the principles of the present disclosure.
Figure 7:
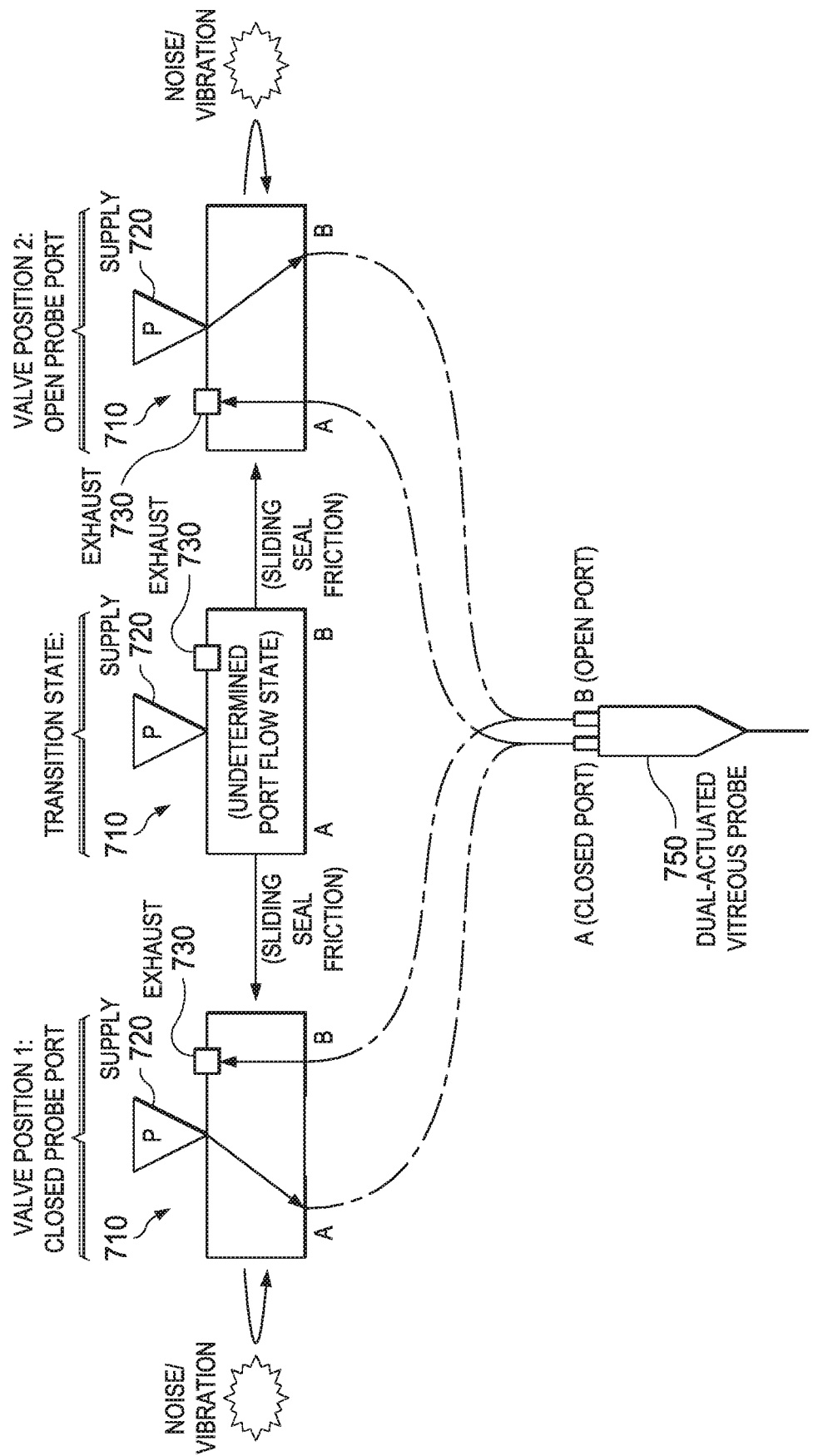
FIG. 7 is a diagram showing an operation of a conventional pneumatic valve.

FIG. 5B is a diagram showing timing sequences during operation of a pneumatic valve according to one embodiment consistent with the principles of the present disclosure. As shown in FIG. 5B, each of the air supply opening 322, air exhaust opening 324, port opening 326 (port "A"), and port opening 328 (port "B") may have independent timing sequence of opening/closing time as the axially symmetric valve body 302 rotates. In some embodiments, the flow grooves may have varying widths or depths to provide variations in flow rate. For example, a gradual increase/decrease in depth or width of a flow groove may correspond to gradual opening or closing of the corresponding channel opening. This may allow gradual and smooth transition between opening and closing of channels to provide smoother actuation at the surgical implement 104.

Figure 6:
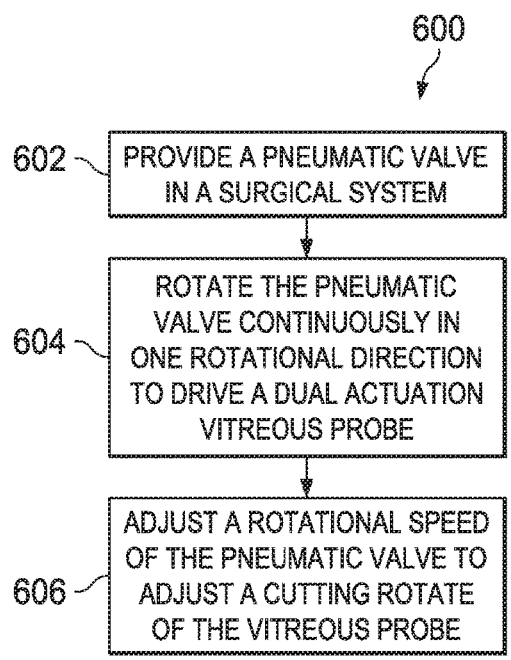
FIG. 6 is a flow chart illustrating a method for operating a pneumatic valve according to an aspect consistent with the principles of the present disclosure.

FIG. 6 is a flow chart illustrating a method 600 for operating a pneumatic valve 300 according to an aspect consistent with the principles of the present disclosure. At 602, a pneumatic valve 300 may be provided in the surgical system 100. The pneumatic valve 300 may be provided at the surgical utility supplying device 102. In some embodiments, the pneumatic valve 300 may be provided at the surgical implement 104. For example, the pneumatic valve 300 may be provided at a reusable portion of the surgical implement 104 or at a consumable portion, such as a part of a single-use surgical implement 104.

In an embodiment, the pneumatic valve 300 may be selected from various types of pneumatic valves that provide different actuation patterns and/or sequences. For example, different types of valves may have different patterns of flow grooves on the axially symmetric valve body to provide various patterns or sequences of actuation. An appropriate type of pneumatic valve may be selected for the specific surgical application or requirement.

At 604, the pneumatic valve 300 may be rotated continuously in one rotational direction to alternate the supply of pressurized air and the release of the air exhaust to the surgical implement 104. In particular, the pneumatic valve 300 may be rotated by a drive shaft 306 driven by a motor. At 606, the rotational speed of the pneumatic valve 300 may be adjusted to adjust an operation rate, such as cutting rate, at the surgical implement. The rotational speed may be controlled or adjusted by the user or by the surgical system based on the application of the surgical operation. The pneumatic valve 300 may alternate the supply of pressurized air and the release of the air exhaust to the surgical implement. In some embodiments, the pneumatic valve 300 also may direct other types of utilities, such as vacuum, compressed air, utility fluid, or the like.

Accordingly, the above embodiments provide a system or method for implementing a pneumatic valve to alternate at least two types of utility supplies to the surgical implement. In particular, the pneumatic valve may include an axially symmetric valve body configured to rotate continuously in one rotational direction to alternate two utility supplies between two input ports of the surgical implement. The rotational pneumatic valve may reduce noise and vibration, as compared to reciprocating valves. The rotational pneumatic valve also may have a frictionless air bearing arrangement that reduces friction and wear of the valve. Further, because there is no reduction in velocity or change in acceleration, the rotational pneumatic valve may allow for higher actuation rate. Flow grooves may be formed on the axially symmetric valve body of the pneumatic valve to provide various actuation patterns and sequences. The shape disclosed herein is illustrated as substantially cylindrical, but the valve body may be formed into any arbitrary, axially symmetric shape.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A surgical system comprising:
   a dual action vitrectomy probe;
   a utility generator configured to supply a pressurized fluid to the dual action vitrectomy probe;
   a fluid exhaust manifold configured to direct a fluid exhaust from the dual action vitrectomy probe;
   a pneumatic valve configured to rotate from a first position in which the pneumatic valve places a first port of the dual action vitrectomy probe in fluid communication with the utility generator and places a second port of the dual action vitrectomy probe in fluid communication with the fluid exhaust manifold, to a second position in which the pneumatic valve places the first port of the dual action vitrectomy probe in fluid communication with the fluid exhaust manifold and the second port of the dual action vitrectomy probe in fluid communication with the utility generator, and the pneumatic valve is configured to rotate within a housing from the second position back to the first position, in one rotational direction;
   wherein the pneumatic valve comprises:
      a valve body; and
      the housing configured to accommodate the valve body, wherein the valve body is configured to rotate within the housing from the first position to the second position and back to the first position in the one rotational direction;
   wherein the housing comprises:
      a chamber configured to accommodate the valve body;
      a first port opening formed on an inner wall of the chamber and in fluid communication with the first port of the dual action vitrectomy probe;
      a second port opening formed on the inner wall of the chamber and in fluid communication with the second port of the dual action vitrectomy probe;
      a fluid pressure opening formed on the inner wall of the chamber and in fluid communication with the utility generator; and
      a fluid exhaust opening formed on the inner wall of the chamber and in fluid communication with the fluid exhaust manifold;
   wherein the valve body comprises:
      a first connection channel configured to place the first port opening and the fluid pressure opening in fluid communication when the valve body is in the first position;
      a second connection channel configured to place the second port opening and the fluid exhaust opening in fluid communication when the valve body is in the first position;
      a third connection channel configured to place the first port opening and the fluid exhaust opening in fluid communication when the valve body is in the second position; and
      a fourth connection channel configured to place the second port opening and the fluid pressure opening in fluid communication when the valve body is in the second position; and
      a drive shaft configured to engage the valve body and to rotate the valve body in the one rotational direction in the housing;
      wherein the valve body is coupled to the drive shaft to receive a rotational driving force from the drive shaft, and wherein the coupling between the valve body and the drive shaft provides radial and tilt compliance between the drive shaft and the valve body.

2. The surgical system of claim 1, wherein the first connection channel, the second connection channel, the third connection channel, and the fourth connection channel are formed through the valve body.

3. The surgical system of claim 2, wherein the valve body further comprises flow grooves formed on a circumferential surface of the valve body and extending from openings of one or more of the first, second, third, or fourth connection channels, wherein the flow grooves keep the first port opening, second port opening, fluid pressure opening, and fluid exhaust openings in fluid communication with the one or more of the first, second, third, or fourth connection channels through portions of the rotation of the valve body to define opening or closing timing sequences between the first port opening, second port opening, fluid pressure opening, and fluid exhaust openings such that a rotational speed of the pneumatic valve corresponds to a cutting rate of the dual actuation vitreous probe.

4. The surgical system of claim 1, wherein the valve body further comprises flow grooves formed on a circumferential surface of the valve body and extending from openings of the one or more of the first, second, third, or fourth connection channels, wherein the flow grooves keep the first port opening, second port opening, fluid pressure opening, and fluid exhaust openings in fluid communication with the one or more of the first, second, third, or fourth connection channels through portions of the rotation of the valve body to define opening or closing timing sequences between the first port opening, second port opening, fluid pressure opening, and fluid exhaust openings such that a rotational speed of the pneumatic valve corresponds to a cutting rate of the dual actuation vitreous probe.

5. The surgical system of claim 1, wherein the utility generator supplies a vacuum.

6. The surgical system of claim 1, wherein a close tolerance air gap is provided between a circumferential surface of the valve body and the inner wall of the chamber to form a frictionless air bearing when the valve body rotates in the housing.

7. The surgical system of claim 1, further comprising concentric air baffles at an opening in the housing in an area of drive shaft entry;

wherein a close tolerance air gap is provided between the circumferential surface of the valve body and the inner wall of the chamber to form a frictionless air bearing when the valve body rotates in the housing, and wherein the close-tolerance air gap and air baffles combine to resist air leakage from the valve body.

8. A surgical system configured to direct a pressurized fluid to and a fluid exhaust from a dual action vitrectomy probe, the surgical system comprising:
  a dual action vitrectomy probe;
  a pneumatic valve comprising:
    a valve body; and
    a housing configured to accommodate the valve body, wherein the valve body is configured to rotate within the housing from a first position, in which the pneumatic valve places a first port of the dual action vitrectomy probe in fluid communication with the pressurized fluid and places a second port of the dual action vitrectomy probe in fluid communication with the fluid exhaust, to a second position, in which the pneumatic valve places the first port of the dual action vitrectomy probe in fluid communication with the fluid exhaust and places the second port of the dual action vitrectomy probe in fluid communication with the pressurized fluid, and the valve body is configured to rotate within the housing from the second position back to the first position while rotating in one rotational direction;
  wherein the housing comprises:
    a chamber configured to accommodate the valve body;
    a first port opening formed on an inner wall of the chamber and in fluid communication with the first port of the dual action vitrectomy probe;
    a second port opening formed on the inner wall of the chamber and in fluid communication with the second port of the dual action vitrectomy probe;
    a fluid pressure opening formed on the inner wall of the chamber and in fluid communication with the pressurized fluid; and
    a fluid exhaust opening formed on the inner wall of the chamber and in fluid communication with the fluid exhaust;
  wherein the valve body comprises:
    a first connection channel configured to place the first port opening and the fluid pressure opening in fluid communication when the valve body is in the first position;
    a second connection channel configured to place the second port opening and the fluid exhaust opening in fluid communication when the valve body is in the first position;
    a third connection channel configured to place the first port opening and the fluid exhaust opening in fluid communication when the valve body is in the second position; and
    a fourth connection channel configured to place the second port opening and the fluid pressure opening in fluid communication when the valve body is in the second position;
  wherein the valve body is configured to engage and receive a rotational driving force from a drive shaft of the surgical system, and wherein the valve body has radial and tilt compliance between the drive shaft and the valve body.

9. The surgical system pneumatic valve of claim 8, wherein the first connection channel, the second connection channel, the third connection channel, and the fourth connection channel are formed through the valve body.

10. The surgical system pneumatic valve of claim 9, wherein the valve body further comprises flow grooves formed on a circumferential surface of the valve body and extending from openings of one or more of the first, second, third, or fourth connection channels, wherein the flow grooves keep the first port opening, second port opening, fluid pressure opening, and fluid exhaust openings in fluid communication with the one or more of the first, second, third, or fourth connection channels through portions of the rotation of the valve body to define opening or closing timing sequences between the first port opening, second port opening, fluid pressure opening, and fluid exhaust openings such that a rotational speed of the pneumatic valve corresponds to a cutting rate of the dual actuation vitreous probe.

11. The surgical system pneumatic valve of claim 8, wherein the valve body further comprises flow grooves formed on a circumferential surface of the valve body and extending from openings of one or more of the first, second, third, or fourth connection channels, wherein the flow grooves keep the first port opening, second port opening, fluid pressure opening, and fluid exhaust openings in fluid communication with the one or more of the first, second, third, or fourth connection channels through portions of the rotation of the valve body to define opening or closing timing sequences between the first port opening, second port opening, fluid pressure opening, and fluid exhaust openings such that a rotational speed of the pneumatic valve corresponds to a cutting rate of the dual actuation vitreous probe.

12. The pneumatic valve of claim 8, wherein a close tolerance air gap is provided between a circumferential surface of the valve body and the inner wall of the chamber to form a frictionless air bearing when the valve body rotates in the housing.

13. A method comprising:
  providing a pneumatic valve in a surgical system to direct a pressurized fluid to and a fluid exhaust from a dual action vitrectomy probe; and
  rotating a valve body of the pneumatic valve in one rotational direction to move the valve body from a first position in which the pneumatic valve places a first port of the dual action vitrectomy probe in fluid communication with the pressurized fluid and a second port of the dual action vitrectomy probe in fluid communication with the fluid exhaust, to a second position, in which the pneumatic valve places the first port of the dual action vitrectomy probe in fluid communication with the fluid exhaust and the second port of the dual action vitrectomy probe in fluid communication with the pressurized fluid, and back to the first position;
  adjusting a rotational speed of the valve body to adjust a cutting rate of the dual actuation vitreous probe;
  wherein the pneumatic valve comprises:
    a housing configured to accommodate the valve body;
    wherein the housing comprises:
      a chamber configured to accommodate the valve body;
      a first port opening formed on an inner wall of the chamber and in fluid communication with the first port of the dual action vitrectomy probe;
      a second port opening formed on the inner wall of the chamber and in fluid communication with the second port of the dual action vitrectomy probe;
      a fluid pressure opening formed on the inner wall of the chamber and in fluid communication with the pressurized fluid; and a fluid exhaust opening formed on the inner wall of the chamber and in fluid communication with the fluid exhaust;

wherein the valve body further comprises flow grooves formed on a circumferential surface of the valve body, wherein the flow grooves define opening or closing timing sequences between the first port opening, second port opening, fluid pressure opening, and fluid exhaust openings such that a rotational speed of the pneumatic valve corresponds to a cutting rate of the dual actuation vitreous probe.

14. The method of claim 13, further comprising rotating the valve body via a driving shaft of the surgical system.

15. The method of claim 13, wherein a first connection channel, a second connection channel, a third connection channel, and a fourth connection channel are formed through the valve body.

16. The method of claim 15, wherein the valve body further comprises the flow grooves formed on a circumferential surface of the valve body and extending from openings of one or more of the first, second, third, or fourth connection channels, wherein the flow grooves keep the first port opening, second port opening, fluid pressure opening, and fluid exhaust openings in fluid communication with the one or more of the first, second, third, or fourth connection channels through portions of the rotation of the valve body to define opening or closing timing sequences between the first port opening, second port opening, fluid pressure opening, and fluid exhaust openings such that the rotational speed of the pneumatic valve corresponds to the cutting rate of the dual actuation vitreous probe.

17. The method of claim 13, wherein the valve body further comprises the flow grooves formed on a circumferential surface of the valve body and extending from openings of one or more of the first, second, third, or fourth connection channels, wherein the flow grooves keep the first port opening, second port opening, fluid pressure opening, and fluid exhaust openings in fluid communication with the one or more of the first, second, third, or fourth connection channels through portions of the rotation of the valve body to define opening or closing timing sequences between the first port opening, second port opening, fluid pressure opening, and fluid exhaust openings such that the rotational speed of the pneumatic valve corresponds to the cutting rate of the dual actuation vitreous probe.

18. The method of claim 13,
wherein a close tolerance air gap is provided between a circumferential surface of the valve body and the inner wall of the chamber to form a frictionless air bearing when the valve body rotates in the housing; and
wherein the valve body is configured to engage and receive a rotational driving force from a drive shaft of the surgical system, and wherein the valve body has radial and tilt compliance between the drive shaft and the valve body.

* * * * *